United States Patent [19]
Parry

[11] Patent Number: 5,016,369
[45] Date of Patent: May 21, 1991

[54] TAG ASSEMBLIES

[75] Inventor: John S. Parry, Stroud, England

[73] Assignee: Sterimatic Holdings Limited, Tortola, British Virgin Isls.

[21] Appl. No.: 600,998

[22] Filed: Oct. 19, 1990

Related U.S. Application Data

[63] Continuation of Ser. No. 892,426, Aug. 4, 1986, abandoned.

[30] Foreign Application Priority Data

Aug. 3, 1985 [GB] United Kingdom ............... 8519557

[51] Int. Cl.$^5$ ................................................ G09F 3/00
[52] U.S. Cl. ................................ 40/301; 119/156; 606/188
[58] Field of Search ................ 119/156; 40/300, 301, 40/302, 303, 304; 606/188, 116, 117, 2, 3, 47, 244, 411, 412; 128/62 A, 316, 330, 333

[56] References Cited

U.S. PATENT DOCUMENTS

| | | | |
|---|---|---|---|
| 4,469,463 | 9/1984 | Van Overloop | 401/196 X |
| 4,635,389 | 1/1987 | Oudelette | 40/301 |

FOREIGN PATENT DOCUMENTS

| | | | |
|---|---|---|---|
| 2487634 | 2/1982 | France | 40/301 |
| 2510205 | 1/1983 | France | 40/301 |

Primary Examiner—Gene Mancene
Assistant Examiner—R. Thomas Price
Attorney, Agent, or Firm—Young & Thompson

[57] ABSTRACT

Male and female tag members have respectively a projecting portion for extending through the part to be tagged and a receiving portion for accommodating an end part of the projecting portion after it has passed through the part to be tagged. The receiving portion is in the form of a closed container defining a cylindrical chamber containing sterilizing substance. The action of fitting the tag assembly to the part to be tagged causes the projecting portion to pierce a weakened portion of a wall of the chamber resulting in release of sterilizing substance from the chamber, for example for sterilizing the wound formed when the assembly is fitted to an animal's ear. In a variant the sterilizing substance is replaced by a substance having active pharmaceutical properties.

1 Claim, 2 Drawing Sheets

TAG ASSEMBLIES

This application is a continuation of application Ser. No. 06/892,426, filed Aug. 4, 1986 abandoned.

This invention relates to tag assemblies, and is more particularly, but not exclusively, concerned with such assemblies for use in the tagging of livestock.

It is a widespread practice for farmers to tag livestock, particularly cattle, as a means of identification and in order to attempt to prevent the cattle from being stolen. A widely used form of tag assembly comprises a male tag member having a projecting portion which is passed through the animal's ear and is then locked in a receiving well in a female tag member. Once inserted in the receiving well the projecting portion cannot be withdrawn, and the receiving well provides some protection against the end of the projecting portion being sawn off to release it from the well. In order to fit such a tag assembly a special tool is used which punctures the animal's ear and forces the projecting portion through the hole so formed. However, there is a danger that infection may be introduced by such a fitting process.

It is an object of the invention to provide an improved tag assembly which decreases the risk of infection being introduced during fitting of the assembly and/or applies a pharmaceutical treatment to the animal and/or serves as a repellant or attractant function.

According to the invention there is provided a male or female tag member of a tag assembly comprising a male tag member having a projecting portion for extending through the part to be tagged, and a female tag member having a receiving portion for receiving an end part of the projecting portion after it has passed through the part to be tagged, which male or female tag member incorporates a substance having specific chemical properties disposed so that said substance is released or activated by the action of fitting of the tag assembly to the part to be tagged.

In a preferred embodiment the substance has sterilising properties so that it sterilises the wound in the animal's ear in the case where the tag assembly is fitted to an animal's ear.

Whilst the word "sterilising" is used in this specification in the sense of killing microorganisms, such as bacteria or viruses, it should be understood that it is not essential that all microorganisms are killed, that is to say that the wound is rendered absolutely sterile. The sterilising substance may, for example, be in the form of a liquid, gel or powder.

The substance may alternatively or additionally have active pharmaceutical properties, in which case the animal may be treated pharamaceutically by release of the substance into the animal's blood by way of the wound formed in the animal's ear on fitting of the assembly, or the substance may be absorbed gradually through the animal's skin.

The use of such a tag assembly incorporating a pharmaceutical substance can be extremely advantageous in practice since it enables an animal to be treated simultaneously with the fitting of a tag assembly, without requiring the animal to be submitted to a separate treatment operation. In this regard the pharmaceutical substance may have anti-parasitic, anti-viral, anti-bacterial, immunilogical or hormonal properties, for example, or a combination of two or more of such properties.

The substance may alternatively or additionally have repellant or attractant properties, and may act directly as an insect repellant or an insecticide.

In a preferred form of the invention the receiving portion of the female member incorporates the substance having specific chemical properties. Conveniently the receiving portion is in the form of a container containing the substance and having a wall which may be pierced so as to enable the end part of the projecting portion to be introduced into the container when the tag assembly is fitted. In this way it may be arranged that, when the wall of the container is pierced, a quantity of substance is ejected from the container so as to sterilise the wound in the animal's ear or so as to treat the animal pharmaceutically.

Preferably the female tag member comprises a main lamina portion and the receiving portion which projects from the lamina portion in the direction away from the male tag member when the male and female tag members are fitted together to form the tag assembly.

In an alternative form of the invention the substance having specific chemical properties may be incorporated in the male tag member instead of the female tag member in which case it may be disposed in a chamber at the base of the projecting portion and may be released, for example, by the piercing part of a fitting tool passing through the chamber before it pierces the animal's ear.

The invention further provides a method of fitting a tag assembly comprising passing a projecting portion of a male tag member through the part to be tagged, and introducing an end part of the projecting portion into a receiving portion of a female tag member, one of said tag members incorporating a substance having specific chemical properties disposed so that said substance is released or activated by the action of fitting of the tag assembly to the part to be tagged.

In order that the invention may be more fully understood, two embodiments of the invention will now be described, by way of example, with reference to the accompanying drawings, in which.

Figure 1:
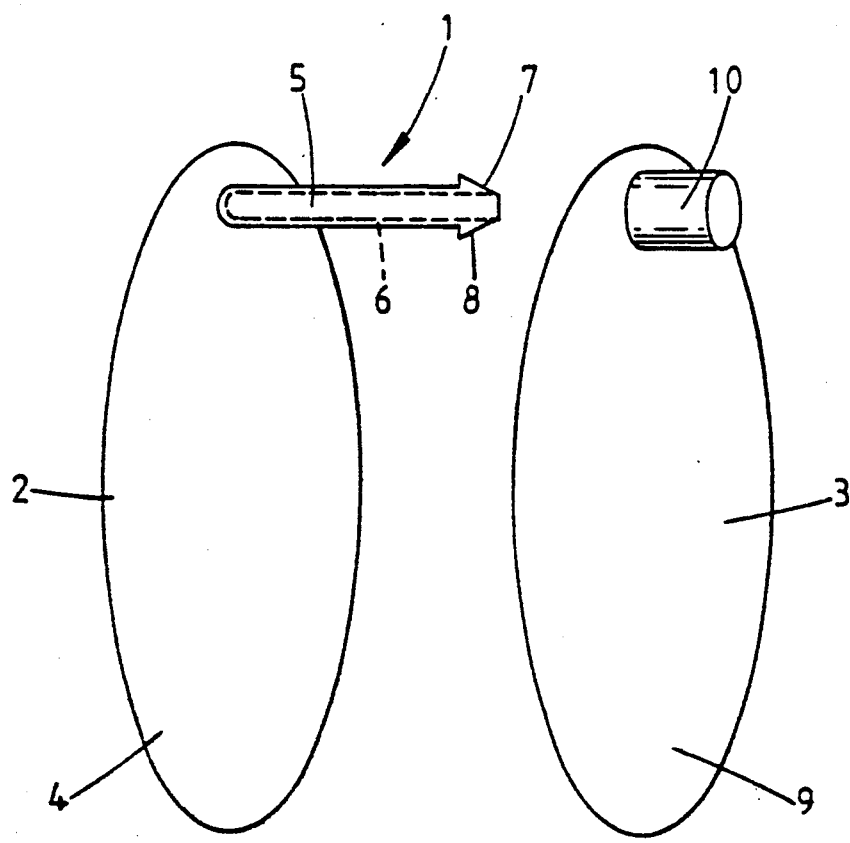
FIG. 1 is a perspective view of male and female tag members of a first embodiment in their disassembled state.
Figure 2:
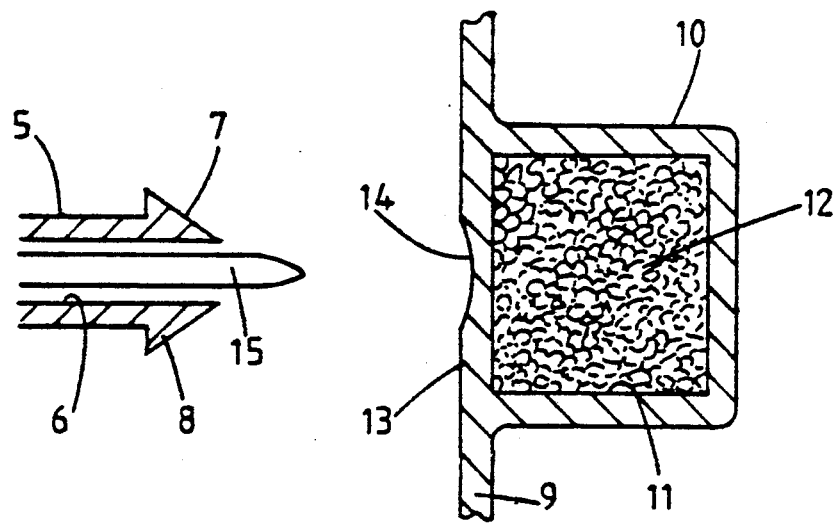
FIG. 2 is a sectional view of parts of the male and female tag members of FIG. 1 on an enlarged scale.

Referring to FIGS. 1 and 2 the tag assembly 1 is intended to be fitted to an animal's ear, and comprises male and female tag members 2 and 3 intended to be disposed on opposite sides of the ear and to be held together by a part passing through the ear, when fitted to the animal. The male member 2 comprises a disc 4 and a projecting portion 5 having a bore 6 (shown in broken lines in FIG. 1) opening at the tip 7 of the projecting portion 5 and also extending through the disc 4 so as to open on the opposite side of the disc 4. The tip 7 of the projecting portion 5 is provided with barbs 8 whose function will become apparent from the description below.

The female tag member 3 comprises a disc 9 and a receiving portion 10 of generally cylindrical form which projects from that surface of the disc 9 which faces away from the male tag member 2 when the tag members 2 and 3 are fitted together to form a tag assembly 1. As may be seen by referring to FIG. 2, the receiving portion 10 is in the form of a closed container defining a cylindrical chamber 11 which contains a sponge 12 impregnated with sterilising substance. Furthermore the container has a wall 13 in the plane of the disc 9 having a weakened portion 14.

When the tag assembly 1 is to be fitted to an animal's ear, a special fitting tool is used having two jaws one of which is provided with a recess in which the receiving portion 10 of the female tag member 3 is received and held by a catch mechanism and the other of which is provided with a piercing part 15 which is inserted in the bore 6 in the projecting portion 5 of the male tag member 2, as shown in FIG. 2. The fitting tool is positioned so that the animal's ear lies between the two jaws and the male and female tag members 2 and 3 engaged by those jaws. The jaws of the tool are then closed so as to cause the tip of the piercing part 15, which projects from the tip 7 of the projecting portion 5 as shown in FIG. 2, to pierce the animal's ear. The hole formed in the animal's ear is then enlarged as the tip 7 of the projecting portion 5 is forced through the ear. The piercing part 15 then pierces the weakened portion 14 of the container wall 13 and passes into the chamber 11 together with the tip 7 of the projecting portion 5. Once the tip 7 has entered the chamber 11, the barbs 8 on the tip 7 prevent this tip 7 being withdrawn from the chamber 11 and accordingly establish a permanent connection between the male and female tag members 2 and 3.

The action of passing the piercing part 15 into the chamber 11 causes the projecting tip of this part 15 to be coated with sterilising substance. The piercing part 15 may then be withdrawn from the bore 6 in the projecting portion 5, and the receiving portion 10 may be released by the fitting tool. This tool may then be used for fitting of tag assemblies to other animals, and the danger of an infection being transmitted by the piercing part 15 of the tool is minimised due to the application of sterilising substance to this part 15.

The action of piercing the weakened portion 14 as the tip of the piercing part 15 and the tip 7 of the projecting portion 5 are introduced into the chamber 11 will also cause compression of the sponge 12 and will result in sterilising substance being squeezed out of the sponge 12 and back through the aperture formed in the weakened portion 14 so as to sterilise the wound formed in the animal's ear.

The tag assembly 1 is made generally of a flexible plastics or rubber material, although the tip 7 of the projecting portion 5 of the male tag member 2 may be strengthened by incorporating a metallic inset.

Figure 3:
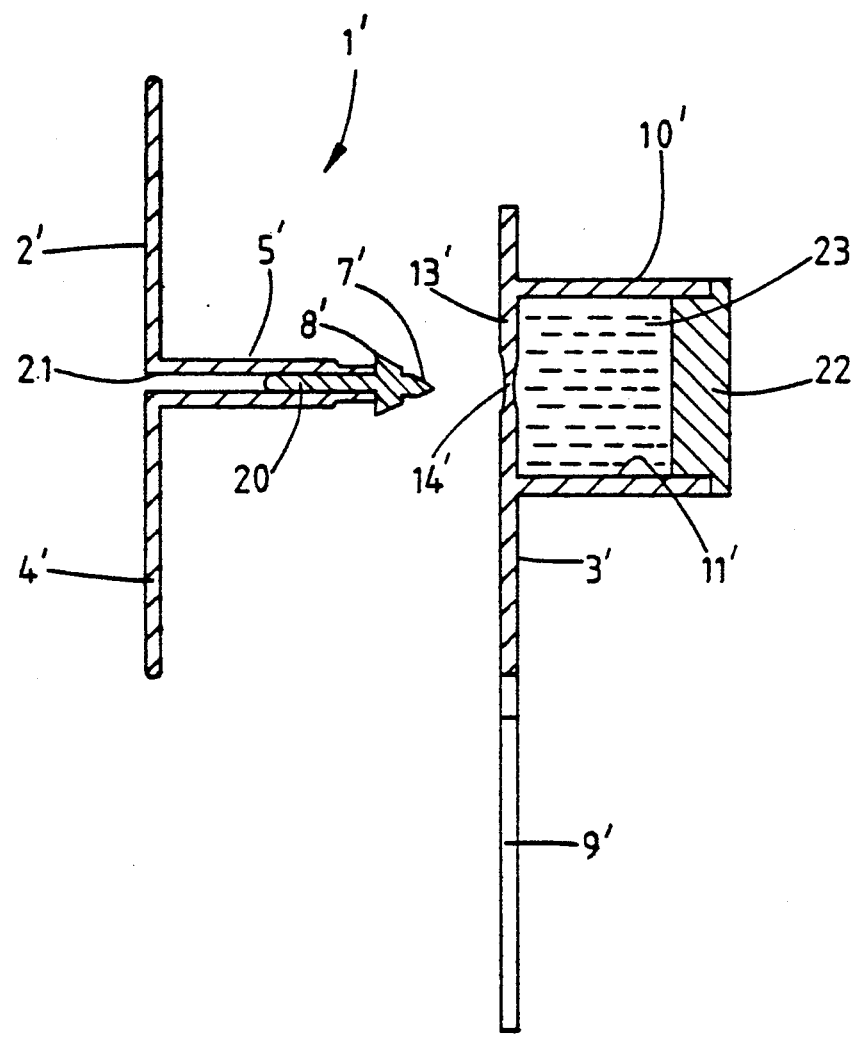
FIG. 3 is a sectional view of male and female tag members of a second embodiment in their disassembled state.

An alternative embodiment in accordance with the invention is shown in FIG. 3.

Similar parts are given the same reference numerals in FIG. 3 as in FIGS. 1 and 2, but with the numerals primed. In this respect the male tag member 2' of this embodiment has a hollow portion 5' projecting from the centre of a circular disc 4', and a brass insert 20 is a force fit within the bore 21 of the projecting portion 5' and defines a tip 7' for piercing the animal's ear. It should be noted that there is no opening at the tip 7' for a piercing part.

The female tag member 3' of the FIG. 3 embodiment has a laminar body portion 9' substantially in the shape of an inverted - T. The lower part of the body portion 9' is not shown in section in the figure in order to illustrate the extent of the cross-bar of this T shape. In this embodiment the receiving portion 10' is closed off by a cap 22 which is ultrasonically welded to the remainder of the receiving portion 10', and a substance 23 having specific chemical properties is accommodated within the cylindrical chamber 11' in the form of a liquid, cream or gel.

This tag assembly is fitted to the animal's ear in a similar manner to the assembly of FIGS. 1 and 2 except that, in this case, the piercing part of the fitting tool is not required and is replaced simply by a locating stud which fits within the bore 21 in the male tag member 2', the piercing of the animal's ear and of the weakened portion 14' of the wall 13' being achieved directly by the tip 7'. The action of piercing the weakened portion 14' causes the substance 23 to flow into the wound. This substance may have various properties as previously discussed, although it is preferred that it should at least act to disinfect the wound and maintain aseptic conditions whilst the wound heals.

It should be understood that, although the whole of the above description is given with reference to the tagging of livestock, the invention is also applicable to tags or jewellery for humans. For example, the invention may be incorporated in earrings to sterilise the wound formed by piercing of the ear, or to release a quantity of perfume.

It will be understood by those skilled in the art that the male and female tag members may be integrally formed at the opposite ends of a flexible strip.

I claim:

1. An animal tag assembly comprising a male tag member having a projecting portion terminating in an enlarged head for extending through the part of the animal to be tagged, a female tag member having a laminar portion and a sealed container projecting from the laminar portion when the male and female tag members are fitted together to form said tag assembly, and a substance having specific chemical properties sealed in said container, said container having a wall confronting said enlarged head immediately prior to the fitting together of said members, said wall maintaining said container sealed until penetrated, and said wall, after being penetrated by said projecting portion, engaging behind said enlarged head to maintain said male member assembled with said female member and to displace said substance from the container back through the aperture formed in said wall by penetration of said projecting portion so as to sterilize the wound formed in the part of the animal tagged.

* * * * *